United States Patent
Houssin et al.

(10) Patent No.: US 7,759,530 B2
(45) Date of Patent: Jul. 20, 2010

(54) MOULDED CATALYST BODIES AND METHOD FOR HYDROGENATION OF CARBONYL COMPOUNDS

(75) Inventors: Christophe Houssin, Mannheim (DE); Henrik Junicke, Mannheim (DE); Andrea Haunert, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 751 days.

(21) Appl. No.: 11/571,766

(22) PCT Filed: Jul. 7, 2005

(86) PCT No.: PCT/EP2005/007337

§ 371 (c)(1),
(2), (4) Date: Jan. 8, 2007

(87) PCT Pub. No.: WO2006/005505

PCT Pub. Date: Jan. 19, 2006

(65) Prior Publication Data

US 2008/0299390 A1    Dec. 4, 2008

(30) Foreign Application Priority Data

Jul. 9, 2004    (DE) ................ 10 2004 033 556

(51) Int. Cl.
  B01J 21/04    (2006.01)
  B01J 23/10    (2006.01)
  B01J 23/28    (2006.01)
  B01J 23/30    (2006.01)
  B01J 23/72    (2006.01)

(52) U.S. Cl. ............... 568/861; 502/303; 502/309; 502/318; 502/322; 502/346; 502/351; 568/862

(58) Field of Classification Search ............ 568/861, 568/862; 502/303, 309, 318, 322, 346, 351
See application file for complete search history.

(56) References Cited

U.S. PATENT DOCUMENTS

| | | | | |
|---|---|---|---|---|
| 3,923,694 A | | 12/1975 | Cornthwaite | |
| 4,384,147 A | * | 5/1983 | Baer et al. | 568/861 |
| 5,008,235 A | * | 4/1991 | Wegman et al. | 502/342 |
| 5,334,779 A | * | 8/1994 | Kuo | 568/864 |
| 5,977,010 A | * | 11/1999 | Roberts et al. | 502/244 |
| 5,990,040 A | | 11/1999 | Hu et al. | |
| 6,787,677 B2 | * | 9/2004 | Koch et al. | 568/862 |
| 7,084,312 B1 | * | 8/2006 | Huber et al. | 568/881 |
| 7,183,438 B2 | * | 2/2007 | Gerlach et al. | 564/397 |
| 7,459,571 B2 | * | 12/2008 | Schlitter et al. | 549/295 |
| 7,510,591 B2 | * | 3/2009 | Huber-Dirr et al. | 75/233 |
| 2008/0071120 A1 | * | 3/2008 | Houssin et al. | 568/864 |
| 2008/0207953 A1 | * | 8/2008 | Houssin et al. | 568/420 |

FOREIGN PATENT DOCUMENTS

| | | |
|---|---|---|
| DE | 256515 | 2/1913 |
| DE | 195 05 347 | 9/1995 |
| DE | 198 09 418 | 9/1999 |
| EP | 0 901 815 | 3/1999 |
| WO | 96 14280 | 5/1996 |
| WO | 2004 085356 | 10/2004 |

* cited by examiner

Primary Examiner—H. (Holly) T Le
(74) Attorney, Agent, or Firm—Oblon, Spivak, McClelland, Maier & Neustadt, L.L.P.

(57) ABSTRACT

The invention relates to a method for hydrogenation of an organic compound comprising at least one carbonyl group, whereby the organic compound is brought into contact with a moulded body in the presence of hydrogen. Said body may be produced by a method in which (i) an oxidic material is prepared, comprising copper oxide, aluminum oxide, and at least one oxide of lanthanum, tungsten, molybdenum, titanium, or zirconium, followed by (ii) addition of powdered metallic copper, copper platelets, powdered cement, graphite, mixtures or a mixture thereof with graphite to the oxidic material and (iii) moulding the mixture from (ii) to give a moulded body, characterised in that the moulded body is in the form of catalyst tablets or catalyst extrudates with a diameter d and/or height h<2.5 mm, catalyst beads with a diameter d<2.5 mm or catalyst honeycomb with a cell diameter $r_z$<2.5 mm.

9 Claims, No Drawings

MOULDED CATALYST BODIES AND METHOD FOR HYDROGENATION OF CARBONYL COMPOUNDS

The invention relates to a process for the catalytic hydrogenation of organic compounds containing at least one carbonyl group in the presence of copper-containing catalyst pellets and the copper-containing shaped catalyst bodies of defined size.

The catalytic hydrogenation of carbonyl compounds such as carboxylic acids or carboxylic esters occupies an important position in the production lines of the basic chemicals industry.

In industrial processes, the catalytic hydrogenation of carbonyl compounds such as carboxylic esters is carried out virtually exclusively in fixed-bed reactors. Fixed-bed catalysts used are, apart from catalysts of the Raney type, especially support catalysts, for example copper, nickel or noble metal catalysts.

U.S. Pat. No. 3,923,694 describes, for example, a catalyst of the copper oxide/zinc oxide/aluminum oxide type. The disadvantage of this catalyst is that it has insufficient mechanical stability during the reaction and therefore disintegrates relatively quickly. This results in a drop in activity and the building-up of a differential pressure over the reactor due to the disintegrating catalyst bodies. As a consequence, the plant has to be shut down prematurely.

DE 198 09 418.3 describes a process for the catalytic hydrogenation of a carbonyl compound in the presence of a catalyst comprising a support, which comprises predominantly titanium dioxide, and, as active component, copper or a mixture of copper with at least one metal selected from the group consisting of zinc, aluminum, cerium, noble metals and metals of transition group VII, with the surface area of copper being not more than 10 m$^2$/g. Preferred support materials are mixtures of titanium dioxide with aluminum oxide or zirconium oxide or aluminum oxide and zirconium oxide. In a preferred embodiment, the catalyst material is shaped with addition of metallic copper powder or copper flakes.

DE-A 195 05 347 describes, quite generally, a process of catalyst pellets having a high mechanical strength, with a metal powder or a powder of a metal alloy being added to the material to be pelletized. Aluminum powder or copper powder or copper flakes, inter alia, is added as metal powder. However, in the case of a copper oxide/zinc oxide/aluminum oxide catalyst, the addition of aluminum powder gives a shaped body which has poorer lateral compressive strength than a shaped body produced without addition of aluminum powder, and, when used as catalyst, the shaped body of the invention displayed a poorer conversion activity than did catalysts produced without addition of aluminum powder. The document likewise discloses a hydrogenation catalyst comprising NiO, ZrO$_2$, MoO$_3$ and CuO, in which Cu powder, inter alia, was mixed during its production. However, this document gives no information on the selectivity or the activity.

DE 256 515 describes a process for preparing alcohols from synthesis gas using catalysts based on Cu/Al/Zn which are obtained by comilling and pelletization with metallic copper powder or copper flakes. The process described is mainly directed at the preparation of mixtures of $C_1$-$C_5$-alcohols, and the process is carried out in a reactor whose upper third contains a catalyst having a relatively high proportion of copper powder or copper flakes and whose lower third contains a catalyst having a lower proportion of copper powder or copper flakes.

It is an object of the present invention to overcome the disadvantages of the prior art and to provide processes for the catalytic hydrogenation of carbonyl compounds and to provide catalysts which have both a high mechanical stability and a high hydrogenation activity and selectivity.

We have found that this object is achieved by simultaneous precipitation of a copper compound, an aluminum compound and at least one lanthanum, tungsten, molybdenum, titanium or zirconium compound, addition of metallic copper powder, copper flakes or cement powder or a mixture thereof or a mixture of these with graphite and subsequent drying, calcination and shaping to form catalyst pellets or catalyst extrudates having a diameter d and/or a height h of <2.5 mm, catalyst spheres having a diameter d of <2.5 mm or honeycombs having a cell diameter $r_z$ of less than 2.5 mm, giving a shaped catalyst body which, due to the addition of at least one lanthanum, tungsten, molybdenum, titanium or zirconium compound, displays high activities and selectivities and has a high stability.

The present invention accordingly provides a process for the hydrogenation of an organic compound containing at least one carbonyl group, which comprises bringing the organic compound in the presence of hydrogen into contact with a shaped body which can be produced by a process in which
(i) an oxidic material comprising copper oxide, aluminum oxide and at least one of the oxides of lanthanum, tungsten, molybdenum, titanium or zirconium, with preference being given to the oxides of lanthanum and/or tungsten, is made available,
(ii) pulverulent metallic copper, copper flakes, pulverulent cement or a mixture thereof or a mixture thereof with graphite can be added to the oxidic material, and
(iii) the mixture resulting from (ii) is shaped to form a catalyst pellet or a catalyst extrudate having a diameter d and/or a height h of <2.5 mm, catalyst spheres having a diameter d of <2.5 mm or catalyst honeycombs having a cell diameter $r_z$ of <2.5 mm.

Among the oxides of lanthanum, tungsten, molybdenum, titanium or zirconium, lanthanum oxide is preferred. The shaped catalyst body contains neither zinc oxide nor nickel oxide.

In preferred embodiments, the shaped bodies of the present invention are used as uniform-composition catalysts, impregnated catalysts, coated catalysts and precipitated catalysts.

The catalyst used in the process of the present invention is produced by precipitating the active component copper, the component aluminum and the component consisting of at least one of the oxides of lanthanum, tungsten, molybdenum, titanium or zirconium either simultaneously or in succession, preferably by means of a sodium carbonate solution, subsequently drying and calcining the precipitate and pelletizing it or pressing it to produce the further shapes and calcining it again.

In particular, the following precipitation method is useful:
A) A copper salt solution, an aluminum salt solution and a solution of at least one salt of lanthanum, tungsten, molybdenum, titanium or zirconium or a solution comprising a copper salt, an aluminum salt and at least one of the salts of lanthanum, tungsten, molybdenum, titanium or zirconium is/are precipitated in parallel or in succession by means of a sodium carbonate solution. The precipitated material is subsequently dried and, if appropriate, calcined,
B) Precipitation of a copper salt solution and a solution of at least one salt of lanthanum, tungsten, molybdenum, titanium or zirconium or a solution comprising a copper salt and at least one salt of lanthanum, tungsten, molybdenum, titanium or zirconium onto a prefabricated aluminum oxide support. In a particularly preferred embodiment, this is present as powder in an aqueous suspension. However, the support material can also be in the form of spheres, honeycombs or pellets.

B1) In an embodiment (I), a copper salt solution and a solution of at least one salt of lanthanum, tungsten, molybdenum, titanium or zirconium or a solution comprising a copper salt and at least one salt of lanthanum, tungsten, molybdenum, titanium or zirconium is/are precipitated, preferably by means of sodium carbonate solution. An aqueous suspension of the support material aluminum oxide is used as initial charge.

Precipitates resulting from A) or B) are filtered and preferably washed free of alkali in a customary manner, as is described, for example in DE 198 09 418.3.

Both the end products from A) and those from B) are dried at from 50 to 150° C., preferably at 120° C. and subsequently calcined if appropriate, preferably for 2 hours at generally from 200 to 600° C., in particular from 300 to 500° C.

As starting materials for A) and/or B), it is in principle known to use all Cu(I) and/or Cu(II) salts which are soluble in the solvents used for application to the support, for example nitrates, carbonates, acetates, oxalates or ammonium complexes, analogous aluminum salts and salts of lanthanum, tungsten, molybdenum, titanium or zirconium. For methods A) and B), particular preference is given to using copper nitrate.

The shaping the component (ii), pulverulent metallic copper, copper flakes, pulverulent cement, a mixture thereof or a mixture thereof with graphite is then added to the oxidic material obtained after precipitation, drying and, if appropriate, calcination.

The dried powder obtained is then shaped to produce the catalyst pellet of the present invention or the catalyst extrudates of the present invention by means of a suitable tableting press or a suitable extruder to form pellets or extrudates having a diameter d of less than 2.5 mm and/or a height h of less than 2.5 mm, preferably d and/or h are less than 2 mm, particularly preferably d and/or h are less than 1.0 mm.

The catalyst of the present invention can also be in the form of catalyst spheres having a diameter d of <2.5 mm, preferably less than 1 mm.

Further suitable shaped catalyst bodies according to the present invention are honeycombs having a cell diameter r, of less than 2.5 mm, preferably less than 1 mm, which can be produced in a known manner from the above-described powder.

The shaped catalyst body of the present invention is preferably used in the form of pellets.

The catalyst pellets can be symmetrical, i.e. height h and diameter d are identical, or unsymmetrical, i.e. height h and diameter d take on different values, but d and/or h are less than 2.5 mm. In the case of the unsymmetrical pellets, the ratio d:h can be up to a maximum of 1:2, i.e. the maximum height of the pellet is twice the diameter of the pellet. In the process of the present invention, particular preference is given to using symmetrical catalyst pellets having a diameter d and a height h of 1.5 mm.

The shaped catalyst bodies of the present invention are heated, preferably for 2 hours, at from 300 to 600° C., in particular from 400 to 500° C. This shaping process allows, compared to the exclusive use of graphite as tableting aid in the customary processes, particularly easy-to-carry out shaping of the powder to form pellets, extrudates, spheres and honeycombs and gives catalysts which are very chemically and mechanically stable.

The composition of the oxidic material is generally such that the proportion of copper oxide is in the range from 40 to 90% by weight, the proportion of oxides of lanthanum, tungsten, molybdenum, titanium or zirconium is in the range from 0 to 50% by weight and the proportion of aluminum oxide is up to 50% by weight, in each case based on the total weight of the abovementioned oxidic constituents, with these three oxides together making up at least 80% by weight of the oxidic material after calcination and cement not being included as part of the oxidic material in the above sense.

In a preferred embodiment, the present invention accordingly provides a process as described in which the oxidic material comprises (a) copper oxide in a proportion in the range $50 \leq x \leq 80\%$ by weight, preferably $55 \leq x \leq 75\%$ by weight, (b) aluminum oxide in a proportion in the range $15 \leq y \leq 35\%$ by weight, preferably $20 \leq y \leq 30\%$ by weight, and (c) at least one of the oxides of lanthanum, tungsten, molybdenum, titanium or zirconium, preferably of lanthanum and/or tungsten, in a proportion in the range $2 \leq z \leq 20\%$ by weight, preferably $3 \leq z \leq 15\%$ by weight, in each case based on the total weight of the oxidic material after calcination, where $80 \leq x+y+z \leq 100$, in particular $95 \leq x+y+z \leq 100$.

The process of the present invention and the catalysts of the present invention are distinguished by the fact that addition of lanthanum, tungsten, molybdenum, titanium or zirconium in the precipitation leads to a high stability of the shaped body used as catalyst.

In general, the amount of pulverulent copper, copper flakes or pulverulent cement or a mixture thereof or a mixture thereof with graphite added to the oxidic material is in the range from 1 to 40% by weight, preferably in the range from 2 to 20% by weight and particularly preferably in the range from 3 to 10% by weight, in each case based on the total weight of the oxidic material.

As cement, preference is given to using an alumina cement. The alumina cement particularly preferably consists essentially of aluminum oxide and calcium oxide, in particular it comprises from about 75 to 85% by weight of aluminum oxide and from about 15 to 25% by weight of calcium oxide. It is also possible to use a cement based on magnesium oxide/aluminum oxide, calcium oxide/silicon oxide and calcium oxide/aluminum oxide/iron oxide.

In particular, the oxidic material may further comprise a proportion of not more than 10% by weight, preferably not more than 5% by weight, based on the total weight of the oxidic material, of at least one additional component selected from the group consisting of the elements Re, Fe, Ru, Co, Rh, Ir, Ni, Pd and Pt.

In a further preferred embodiment of the process of the invention, graphite is added to the oxidic material prior to shaping to form the shaped body if it comprises copper powder, copper flakes or cement powder or the mixture thereof. Preference is given to adding such an amount of graphite that shaping to form a shaped body can be carried out more readily. In a preferred embodiment, from 0.5 to 5% by weight of graphite, based on the total weight of the oxidic material, is added. Here, it is immaterial whether the graphite is added to the oxidic material before or after or simultaneously with the copper powder, the copper flakes or the cement powder or the mixture thereof.

The present invention accordingly also provides a process as described above in which graphite in an amount of from 0.5 to 5% by weight, based on the total weight of the oxidic material, is added to the oxidic material or the mixture of copper, copper flakes and/or cement resulting from (ii).

In a preferred embodiment, the present invention therefore furthermore also provides a shaped body comprising an oxidic material comprising (a) copper oxide in a proportion in the range $50 \leq x \leq 80\%$ by weight, preferably $55 \leq x \leq 75\%$ by weight, (b) aluminum oxide in a proportion in the range $15 \leq y \leq 35\%$ by weight, preferably $20 \leq y \leq 30\%$ by weight, and (c) at least one of the oxides of lanthanum, tungsten, molybdenum, titanium or zirconium, preferably of the oxides of lanthanum and/or tungsten, in a proportion in the range $2 \leq z \leq 20\%$ by weight, preferably $3 \leq z \leq 15\%$ by weight, in each case based on the total weight of the oxidic material after calcination, where $80 \leq x+y+z \leq 100$, in particular $95 \leq x+y+z \leq 100$, metallic copper powder, copper flakes or cement powder or a mixture thereof in a proportion in the range from 1 to 40% by weight, based on the total weight of the oxidic material, and graphite in a proportion of from 0.5 to 5% by weight, based on the total weight of the oxidic material, where the sum of the proportions of oxidic material, metallic copper powder, copper flakes or cement powder or a mixture thereof and graphite makes up at least 95% by weight of the shaped body, wherein the shaped body is in the form of a catalyst pellet or catalyst extrudate having a diameter d and/or a height h of <2.5 mm, catalyst spheres having a diameter d of <2.5 mm or catalyst honeycombs having a cell diameter $r_z$ of <2.5 mm. In this preferred embodiment, too, the shaped body is free of zinc oxide and nickel oxide.

After addition of the copper powder, the copper flakes or the cement powder or the mixture thereof and, if desired, graphite to the oxidic material, the shaped body obtained after shaping is, if desired, calcined at least once for a period of generally from 0.5 to 10 hours, preferably from 0.5 to 2 hours. The temperature in this calcination step or steps is generally in the range from 200 to 600° C., preferably in the range from 250 to 500° C. and particularly preferably in the range from 270 to 400° C.

In the case of shaping using cement powder, it may be advantageous to moisten the shaped body obtained before calcination with water and subsequently to dry it.

When the shaped body is used as catalyst in the oxidic form, it is prereduced by means of reducing gases, for example hydrogen, preferably hydrogen/inert gas mixtures, in particular hydrogen/nitrogen mixtures, at from 100 to 500° C., preferably from 150 to 350° C. and in particular from 180 to 200° C., prior to being brought into contact with the hydrogenation solution. This is preferably carried out using a mixture having a hydrogen content in the range from 1 to 100% by volume, particularly preferably in the range from 1 to 50% by volume.

In a preferred embodiment, the shaped body of the invention is activated in a manner known per se by treatment with reducing media prior to use as catalyst. The activation is carried out either beforehand in a reduction oven or after installation in the reactor. If the reactor has been activated beforehand in the reduction oven, it is installed in the reactor and supplied directly with the hydrogenation solution under hydrogen pressure.

A preferred area of application of the shaped bodies produced by the process of the present invention is the hydrogenation of organic compounds containing carbonyl groups in a fixed bed. However, other embodiments such as a fluidized-bed reaction using catalyst material in upward and downward swirling motion are likewise possible. The hydrogenation can be carried out in the gas phase or in the liquid phase. The hydrogenation is preferably carried out in the liquid phase, for example in the downflow mode or upflow mode.

When the hydrogenation is carried out in the downflow mode, the liquid starting material comprising the carbonyl compound to be hydrogenated is allowed to trickle over the catalyst bed in the reactor which is under hydrogen pressure, forming a thin liquid film on the catalyst. On the other hand, when the hydrogenation is carried out in upflow mode, hydrogen is introduced into the reactor flooded with the liquid reaction mixture and the hydrogen passes through the catalyst as rising gas bubbles.

In one embodiment, the solution to be hydrogenated is pumped over the catalyst bed in a single pass. In another embodiment of the process of the present invention, part of the product is continuously taken off as product stream after passing through the reactor and, if desired, is passed through a second reactor as defined above. The other part of the product is combined with fresh starting material comprising the carbonyl compound and fed back into the reactor. This mode of operation will hereinafter be referred to as the circulation mode.

If the downflow mode is chosen as embodiment of the present invention, the circulation mode is preferred. Further preference is given to carrying out the hydrogenation in the circulation mode using a main reactor and an after-reactor.

The process of the present invention is suitable for the hydrogenation of carbonyl compounds such as aldehydes and ketones, carboxylic acids, carboxylic esters or carboxylic anhydrides to give the corresponding alcohols, with preference being given to aliphatic and cycloaliphatic, saturated and unsaturated carbonyl compounds. In the case of aromatic carbonyl compounds, formation of undesirable by-products by hydrogenation of the aromatic ring may occur. The carbonyl compounds may bear further functional groups such as hydroxyl or amino groups. Unsaturated carbonyl compounds are generally hydrogenated to the corresponding saturated alcohols. The term "carbonyl compounds" used in the context of the invention encompasses all compounds containing a $C=O$ group, with the exception of inorganic compounds such as carbon monoxide and carbon dioxide, including carboxylic acids and their derivatives. Of course, it is also possible to hydrogenate mixtures of two or more carbonyl compounds. Furthermore, each individual carbonyl compound to be hydrogenated can also contain more than one carbonyl group.

The process of the present invention is preferably used for the hydrogenation of aliphatic aldehydes, hydroxyaldehydes, ketones, acids, esters, anhydrides, lactones and sugars.

Preferred aliphatic aldehydes are branched and unbranched, saturated and/or unsaturated aliphatic $C_2$-$C_{30}$-aldehydes, which are obtainable, for example, by means of the oxo process from linear or branched olefins having internal or terminal double bonds. It is also possible to hydrogenate oligomeric compounds containing more than 30 carbonyl groups.

Examples of aliphatic aldehydes are:

formaldehyde, propionaldehyde, n-butyraldehyde, isobutyraldehyde, valeraldehyde, 2-methylbutyraldehyde, 3-methylbutyraldehyde (isovaleraldehyde), 2,2-dimethyl-propionaldehyde (pivalaldehyde), caproaldehyde, 2-methylvaleraldehyde, 3-methyl-valeraldehyde, 4-methylvaleraldehyde, 2-ethylbutyraldehyde, 2,2-dimethyl-butyraldehyde, 3,3-dimethylbutyraldehyde, caprylic aldehyde, capric aldehyde, glutaraldehyde.

Apart from the short-chain aldehydes mentioned, long-chain aliphatic aldehydes as can be obtained, for example, by means of the oxo process from linear α-olefins, are also particularly suitable.

Particular preference is given to enalization products such as 2-ethylhexenal, 2-methylpentenal, 2,4-diethyloctenal or 2,4-dimethylheptenal.

Preferred hydroxyaldehydes are $C_3$-$C_{12}$-hydroxyaldehydes as are obtainable, for example, from aliphatic and cycloaliphatic aldehydes and ketones by aldol reaction with themselves or formaldehyde. Examples are 3-hydroxypropanal, dimethylolethanal, trimethylol-ethanal (pentaerythrital), 3-hydroxybutanal (acetaldol), 3-hydroxy-2-ethyl-hexanal (butyl aldol), 3-hydroxy-2-methylpentanal (propene aldol), 2-methylolpropanal, 2,2-dimethylolpropanal, 3-hydroxy-2-methylbutanal, 3-hydroxypentanal, 2-methylol-butanal, 2,2-dimethylolbutanal, hydroxypivalaldehyde. Particular preference is given to hydroxypivalaldehyde (HPA) and dimethylolbutanal (DMB).

Preferred ketones are acetone, butanone, 2-pentanone, 3-pentanone, 2-hexanone, 3-hexanone, cyclohexanone, isophorone, methyl isobutyl ketone, mesityl oxide, acetophenone, propiophenone, benzophenone, benzal-acetone, dibenzalacetone, benzalacetophenone, 2,3-butanedione, 2,4-pentanedione, 2,5-hexanedione and methyl vinyl ketone.

Furthermore, carboxylic acids and derivatives thereof, preferably those having 1-20 carbon atoms, can be reacted. In particular, the following may be mentioned:

carboxylic acids such as formic acid, acetic acid, propionic acid, butyric acid, isobutyric acid, n-valeric acid, trimethylacetic acid ("pivalic acid"), caproic acid, enanthic acid, caprylic acid, capric acid, lauric acid, myristic acid, palmitic acid, stearic acid, acrylic acid, methacrylic acid, oleic acid, elaidic acid, linoleic acid, linolenic acid, cyclohexane-carboxylic acid, benzoic acid, phenylacetic acid, o-toluic acid, m-toluic acid, p-toluic acid, o-chlorobenzoic acid, p-chlorobenzoic acid, o-nitrobenzoic acid, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid;

carboxylic esters such as the $C_1$-$C_{10}$-alkyl esters of the abovementioned carboxylic acids, in particular methyl formate, ethyl acetate, butyl butyrate, dialkyl esters of phthalic acid, isophthalic acid, terephthalic acid, adipic acid and maleic acid, e.g. the dimethyl esters of these acids, methyl (meth) acrylate, butyrolactone, caprolactone and polycarboxylic esters, e.g. polyacrylic and polymethacrylic esters and their copolymers, and polyesters, e.g. polymethyl methacrylate or terephthalic esters, and other industrial plastics; in these cases, the reactions carried out are, in particular, hydrogenolyses, i.e. the reaction of esters to form the corresponding acids and alcohols;

fats;

carboxylic anhydrides such as the anhydrides of the abovementioned carboxylic acids, in particular acetic anhydride, propionic anhydride, benzoic anhydride and maleic anhydride;

carboxamides such as formamide, acetamide, propionamide, stearamide, terephthalamide.

It is also possible for hydroxycarboxylic acids e.g. lactic malic, tartaric or citric acid, or amino acids e.g. glycine, alanine, proline and arginine, and peptides to be reacted.

As particularly preferred organic compounds saturated or unsaturated carboxylic acids carboxylic esters carboxylic anhydrides or lactones or mixtures of two or more thereof are hydrogenated.

The present invention therefore also provides a process as described above in which the organic compound is a carboxylic acid, a carboxylic ester a carboxylic anhydride or a lactone.

Examples of these compounds are, inter alia, maleic acid, maleic anhydride, succinic acid, succinic anhydride, adipic acid, 6-hydroxycaproic acid, 2-cyclododecylpropionic acid, the esters of the abovementioned acids, for example the methyl, ethyl, propyl or butyl ester. Further examples are γ-butyrolactone and caprolactone.

In a very particularly preferred embodiment, the present invention provides a process as described above in which the organic compound is adipic acid or an ester of adipic acid.

The carbonyl compound to be hydrogenated can be fed to the hydrogenation reactor either alone or as a mixture with the product of the hydrogenation reaction and can be fed in undiluted form or using an additional solvent. Suitable additional solvents are, in particular, water and alcohols such as methanol, ethanol and the alcohol formed under the reaction conditions. Preferred solvents are water, THF and NMP; particular preference is given to water.

The hydrogenation both in the upflow mode and in the downflow mode, in each case preferably in the circulation mode, is generally carried out at from 50 to 350° C., preferably from 70 to 300° C., particularly preferably from 100 to 270° C., and a pressure in the range from 3 to 350 bar, preferably in the range from 5 to 330 bar, particularly preferably in the range from 10 to 300 bar.

In a very particularly preferred embodiment, the catalysts of the present invention are used in processes for preparing hexanediol and/or caprolactone, as are described in DE 196 07 954, DE 196 07 955, DE 196 47 348 and DE 196 47 349.

High conversions and selectivities are achieved in the process of the present invention using the catalysts of defined size and shape of the present invention. At the same time, the catalysts of the present invention have a high chemical and mechanical stability.

The mechanical stability of solid-state catalysts and specifically the catalysts of the present invention is described by the parameter lateral compressive strength in various states (oxidic, reduced, reduced and suspended under water).

The lateral compressive strength was determined for the purposes of the present patent application by means of a "Z 2.5/T 919" instrument of Zwick (Ulm). In the case of both the reduced catalysts and the used catalysts, the measurement were carried out under a nitrogen atmosphere so as to avoid reoxidation of the catalysts.

The following examples illustrate the invention.

EXAMPLES

Example 1

Production of Catalyst 1

Production of the Catalyst

A mixture of 12.41 kg of a 19.34% strength copper nitrate solution, 14.78 kg of an 8.12% strength aluminum nitrate solution and 1.06 kg of a 37.58% strength lanthanum nitrate× $6H_2O$ solution was dissolved in 1.5 l of water (solution 1). Solution 2 comprises 60 kg of a 20% strength anhydrous $Na_2CO_3$. Solution 1 and solution 2 are fed via separate lines into a precipitation vessel which is provided with a stirrer and contains 10 l of water which has been heated to 60° C. Here, the pH was brought to 6.2 by appropriate adjustment of the feed rates of solution 1 and solution 2.

While keeping the pH constant at 6.2 and the temperature constant at 60° C. all of the solution 1 was reacted with sodium carbonate. The suspension formed in this way was subsequently stirred for another 1 hour. The suspension is filtered and washed with distilled water until the nitrate content of the washings was <10 ppm.

The filter cake was dried at 120° C. for 16 hours and subsequently calcined at 300° C. for 2 hours. The catalyst powder obtained in this way is precompacted with 1% by weight of graphite. The compact obtained is mixed with 5% by weight of Cu flakes from Unicoat and subsequently with 2% by weight of graphite and pressed to form pellets having a diameter of 1.5 mm and a height of 2 mm. The pellets were finally calcined at 350° C. for 2 hours.

The catalyst produced in this way has the chemical composition 57% CuO/28.5% $Al_2O_3$/9.5% $La_2O_3$/5% Cu.

The lateral compressive strength in the oxidic state was 44 N, and that in the reduced state was 25 N, as shown in Table 1.

Example 2

Hydrogenation of Dimethyl Adipate Over Catalyst 1

Dimethyl adipate was hydrogenated continuously in the downflow mode with recirculation (feed/recycle ratio=10/1) at a WHSV of 0.3 kg/(l*h), a pressure of 200 bar and reaction temperatures of 200° C. in a vertical tube reactor charged with 200 ml of catalyst 1. The experiment was carried out for a total time of 7 days. GC analysis found ester conversions of 99% and a hexanediol selectivity of 96.9% in the reaction product at 190° C. After removal from the reactor, the catalyst was found to be still completely intact and had a high mechanical stability. The experimental results are summarized in Table 1.

Example 3

Production of the Comparative Catalyst without Iron

The comparative catalyst was produced using a method analogous to that for catalyst 1, but was pressed to form pellets having a diameter of 3 mm and a height of 3 mm.

The catalyst produced in this way has the chemical composition 57% CuO/28.5% $Al_2O_3$/9.5% $La_2O_3$/5% Cu. The lateral compressive strength in the oxidic and reduced states is shown in Table 1.

Example 4

Hydrogenation of Dimethyl Adipate Over the Comparative Catalyst

Dimethyl adipate was hydrogenated continuously in the downflow mode with recirculation (feed/recycle ratio=10/1) at a WHSV of 0.3 kg/(l*h), a pressure of 200 bar and reaction temperatures of 200° C. in a vertical tube reactor charged with 200 ml of catalyst. The experiment was carried out for a total time of 7 days. GC analysis found ester conversions of 92.4% in each case and hexanediol contents of 88.8% in the reaction product at 220° C. and 240° C., respectively. After removal from the reactor, the catalyst was found to be still completely intact and had a high mechanical stability. The experimental results are summarized in Table 1.

The data in Table 1 below show that the catalysts of the present invention have considerably higher hydrogenation activities, i.e. higher conversions of dimethyl adipate, at 200° C. than the comparative catalyst, and also give higher selectivities to the desired product, i.e. higher contents of the target products hexanediol in the output from the reactor.

TABLE 1

| Catalyst | Reaction temperature [° C.] | Conversion of dimethyl adipate [%] | Hexanediol selectivity [%] | Lateral compressive strength (N) oxid./red. |
|---|---|---|---|---|
| Catalyst 1 | 200 | 99 | 96.9 | 44/25 |
| Comparative catalyst | 200 | 92.4 | 88.8 | 117/87 |

We claim:

1. A process for the hydrogenation of an organic compound containing at least one carbonyl group, said process comprising bringing the organic compound, in the presence of hydrogen, into contact with a shaped body which is produced by a process comprising:
   mixing (i) an oxidic material comprising copper oxide, aluminum oxide and at least one oxide selected from the group consisting of lanthanum, tungsten, molybdenum, titanium and zirconium, and (ii) pulverulent metallic copper, copper flakes, and pulverulent cement, or a mixture thereof with graphite, to form a catalyst mixture, and then
   shaping the catalyst mixture to form a catalyst pellet or a catalyst extrudate having a diameter d and/or a height h of <2.5 mm, catalyst spheres having a diameter d of <2.5 mm, or catalyst honeycombs having a cell diameter $r_z$ of <2.5 mm;
   with the proviso that the shaped body does not contain one or both of zinc oxide and nickel oxide.

2. The process as claimed in claim 1, wherein the oxidic material comprises
   (a) 50-80 wt % copper oxide,
   (b) 15-35 wt % aluminum oxide, and
   (c) 2-20 wt % of at least one oxide selected from the group consisting of lanthanum, tungsten, molybdenum, titanium and zirconium,
   wherein the summation of (a), (b) and (c) is 80-100 wt % based on the total weight of the oxidic material after calcination, and wherein cement is not included as part of the oxidic material.

3. The process as claimed in claim 2, wherein the oxidic material comprises:
   (a) 55-75 wt % copper oxide;
   (b) 20-30 wt % aluminum oxide; and
   (c) 3-15 wt % of at least one oxide selected from the group consisting of lanthanum, tungsten, molybdenum, titanium and zirconium;
   wherein the summation of (a), (b) and (c) is 95-100 wt % based on the total weight of the oxidic material after calcination, and wherein cement is not included as part of the oxidic material.

4. The process as claimed in claim 1, wherein the pulverulent metallic copper, the copper flakes, and the pulverulent cement, or the mixture thereof with graphite, is added in an amount of from 1 to 40% by weight, based on the total weight of the oxidic material.

5. The process as claimed in claim 1, wherein graphite is added in an amount of from 0.5 to 5% by weight, based on the total weight of oxidic material, to the oxidic material or the catalyst mixture.

6. The process as claimed in claim 1, wherein the organic compound is a carboxylic acid, a carboxylic ester, a carboxylic anhydride or a lactone.

7. The process as claimed in claim 6, wherein the organic compound is adipic acid or an ester of adipic acid.

8. A shaped body comprising:
   an oxidic material comprising
   (a) 50-80 wt % copper oxide,
   (b) 15-35 wt % aluminum oxide, and
   (c) 2-20 wt % of at least one oxide selected from the group consisting of lanthanum, tungsten, molybdenum, titanium and zirconium,
   wherein the summation of (a), (b) and (c) is 80-100 wt % based on the total weight of the oxidic material after calcination,
   1-40 wt % of metallic copper powder, copper flakes, and cement powder or a mixture thereof with graphite, based on the total weight of the oxidic material, and
   5-5 wt % graphite, based on the total weight of the oxidic material,
   wherein the sum of the proportions of the oxidic material, the metallic copper powder, the cement powder, and the mixture thereof with graphite, makes up at least 95% by weight of the shaped body, and
   wherein the shaped body is in the form of a catalyst pellet or catalyst extrudate having a diameter d and/or a height h of <2.5 mm, catalyst spheres having a diameter d of <2.5 mm, or catalyst honeycombs having a cell diameter $r_z$ of <2.5 mm,
   with the proviso that the shaped body does not contain one or both of zinc oxide and nickel oxide.

9. The shaped body as claimed in claim 8, wherein the oxidic material comprises:
   (a) 55-75 wt % copper oxide;
   (b) 20-30 wt % aluminum oxide; and
   (c) 3-15 wt % of at least one oxide selected from the group consisting of lanthanum, tungsten, molybdenum, titanium and zirconium;
   wherein the summation of (a), (b) and (c) is 95-100 wt %, based on the total weight of the oxidic material after calcination.

* * * * *